United States Patent
Yang et al.

(10) Patent No.: US 12,062,414 B1
(45) Date of Patent: Aug. 13, 2024

(54) **SYSTEM AND METHOD FOR PREDICTING SUSCEPTIBILITY OF GENUS *KLEBSIELLA* TO AMIKACIN**

(71) Applicants: Peking Union Medical College Hospital, Chinese Academy of Medical Sciences, Beijing (CN); Hangzhou Matridx Biotechnology Co Ltd, Hangzhou (CN)

(72) Inventors: Qiwen Yang, Beijing (CN); Jing Chen, Hangzhou (CN); Wei Yu, Beijing (CN); Jun Wang, Hangzhou (CN); Xiaobing Chu, Beijing (CN); Shiyu Chen, Beijing (CN); Qian Zhang, Beijing (CN); YiQun Mi, Hangzhou (CN)

(73) Assignees: Peking Union Medical College Hospital, Chinese Academy of Medical Sciences, Beijing (CN); Hangzhou Matridx Biotechnology Co Ltd, Hangzhou (CN)

( * ) Notice: Subject to any disclaimer, the term of this patent is extended or adjusted under 35 U.S.C. 154(b) by 0 days.

(21) Appl. No.: 18/509,632

(22) Filed: Nov. 15, 2023

(30) Foreign Application Priority Data

Feb. 6, 2023 (CN) .......................... 202310065146.3

(51) Int. Cl.
| | | |
|---|---|---|
| *G01N 33/48* | (2006.01) | |
| *C12N 1/20* | (2006.01) | |
| *G06F 17/18* | (2006.01) | |
| *G16B 10/00* | (2019.01) | |
| *C12R 1/22* | (2006.01) | |

(52) U.S. Cl.
CPC ............. *G16B 10/00* (2019.02); *C12N 1/205* (2021.05); *G06F 17/18* (2013.01); *C12R 2001/22* (2021.05)

(58) Field of Classification Search
None
See application file for complete search history.

(56) References Cited

PUBLICATIONS

CNIPA, Notification of First Office Action for CN202310065146.3, Apr. 11, 2023.
Beijing Union Medical College Hospital of the Chinese Academy of Medical Sciences and Hangzhou Jieyi Biotechnology Co., Ltd (Applicants), Reply to Notification of First Office Action for CN202310065146.3, w/ replacement claims, Apr. 13, 2023.
Beijing Union Medical College Hospital of the Chinese Academy of Medical Sciences and Hangzhou Jieyi Biotechnology Co., Ltd (Applicants), Supplemental Reply to Notification of First Office Action for CN202310065146.3, w/ (allowed) replacement claims, Apr. 14, 2023.
CNIPA, Notification to grant patent right for invention in CN202310065146.3, Apr. 23, 2023.

*Primary Examiner* — Anna Skibinsky

(57) ABSTRACT

A system and a method for predicting susceptibility of genus *Klebsiella* to amikacin are provided. The system includes a calculating unit containing a computer-readable storage medium stored with a computer program; the computer program is used to, when is executed by a processor, implement a calculation method for an Exp(−k) power value, and the calculation method for the Exp(−k) power value includes: step 1, calculating a k value according to formula I; and step 2, calculating the Exp(−k) power value with an Euler's constant e as a base and a −k value as an exponential; and C1 to C5 are respectively copy numbers of an arr-2 gene, an acrB gene, an armA gene, an oqxB gene, and a rmtB gene in to-be-predicted *Klebsiella* strains. When the method and the system are adopted to predict the susceptibility of the genus *Klebsiella* to amikacin, an accuracy rate is about 98.8%.

7 Claims, 2 Drawing Sheets

SYSTEM AND METHOD FOR PREDICTING SUSCEPTIBILITY OF GENUS *KLEBSIELLA* TO AMIKACIN

TECHNICAL FIELD

The disclosure relates to the field of molecular biological technologies, particularly to a system and a method for predicting susceptibility of genus *Klebsiella* to amikacin.

BACKGROUND

Antibiotics used to be a "secret weapon" for human beings to fight against many diseases. At the end of the 19th century and the beginning of the 20th century, human life is greatly improved because of developing a series of antibiotics. In recent years, a wide application range of the antibiotics gradually causes drug abuse, clinical antibiotic resistance and adverse reactions to the antibiotics have thereby been increased, bringing a heavy burden to the global economy. Therefore, it is of great significance to effectively control an abuse of the antibiotics in medical treatment in view of a global problem of the antibiotic resistance.

Pathogenic microorganisms refer to microorganisms, or pathogens, that are capable of invading human bodies and causing infection or even infectious diseases. The pathogenic microorganisms mainly include bacteria, viruses, fungi, parasites, *mycoplasma, chlamydia, rickettsia*, spirochete, etc. There are numerous types of microbial samples. For example, intestinal samples include feces, mucosas, etc.; liquid samples include urine, blood, cerebrospinal fluid, saliva, sputum, alveolar lavage fluid, amniotic fluid, etc.; swab samples include oral cavity, reproductive tract, skin, etc.; and other samples include tissues, liver, eyes, placenta, etc.

Genus *Klebsiella*, whose Latin name is *Klebsiella* Trevisan and a phylogenetic systematics level of which is genus, is straight *bacillus*, with a diameter of 0.3 micrometers (μm) to 1.0 μm and a length of 0.6 μm to 6.0 μm. The genus *Klebsiella* is arranged in a single form, a paired form, or a short chain. Specifically, species (also referred as to strains) of this genus that have been reported so far include *Klebsiella pneumoniae, Klebsiella aerogenes, Klebsiella oxytoca, Klebsiella quasipneumoniae, Klebsiella variicola, Klebsiella michiganensis*, etc.

Specially, the *Klebsiella pneumoniae*, as a type genus (strain) of the genus *Klebsiella*, is widely present in the environment and easily colonizes at a respiratory tract and an intestinal tract of a patient. The *Klebsiella pneumoniae* is a common opportunistic pathogen that causes multi-site infection such as a digestive tract, a respiratory tract, blood, etc., and is one of the pathogens causing human pneumonia and one of common drug-resistant bacteria in hospitals. According to a research of the Naval Medical University of China, a resistance rate of a carbapenem-resistant *Klebsiella pneumoniae* isolated from 2014-2017 to amikacin ($C_{22}H_{43}N_5O_{13}$) is 62.5% (data from 252/403).

The amikacin is an aminoglycoside antibiotic for treating a variety of bacterial infections and plays an antibacterial role by binding to 30 S ("S" refers to a unit of density called the Svedberg unit) subunit of a bacterium to block protein synthesis of the bacterium. Moreover, the amikacin is commonly used for treating hospital-acquired infections caused by gram-negative bacilli with a severe multi-drug resistance, such as *Pseudomonas aeruginosa, acinetobacter*, enterobacteriaceae, etc. When treating a patient with neutrophil deficiency complicated by fever, the amikacin is often used in conjunction with beta-lactam drugs.

An antibiotic susceptibility testing is the most commonly used antibiotic resistance detection method in clinical and laboratory in the worldwide, including disk diffusion test (also referred to as Kirby-Bauer method), an agar dilution method, a broth dilution method, a concentration gradient method, etc.; specially, except for the disk diffusion susceptibility test, other methods can obtain relatively accurate minimum inhibitory concentration (MIC). Moreover, the antibiotic susceptibility testing first needs to obtain a pure culture, which is not suitable for difficult to culture and non-culture bacteria, and spends a lot of time. Therefore, the antibiotic susceptibility testing sometimes is difficult to meet the requirements of rapid diagnosis and symptomatic treatment of current clinical severe and acute infections. Traditional detection and identification methods of the pathogenic microorganisms fail to meet the comprehensive requirements of wide coverage, rapidness and accuracy. In addition, the diagnosis and treatment of infectious diseases are mainly based on empirical and directional methods, and clinicians and patients urgently need innovative detection methods to identify infectious agents more comprehensively, accurately and quickly, assist diagnosis and rational and standardized medication treatment, shorten the course of treatment, reduce the fatality rate, and reduce medical cost.

With a promotion of emerging technologies such as polymerase chain reaction (PCR), whole-genome sequencing, microfluidics, VITEK-2® compact fully-automated bacterial identification/antibiotic susceptibility testing system, etc., and a deep exploration of new technologies for the antibiotic resistance detection, the various technologies for the antibiotic resistance detection are increasingly mature. Although the VITEK-2® compact fully-automated bacterial identification/antibiotic susceptibility testing system is simple, convenient and rapid to operate, its accuracy for identification/antibiotic susceptibility testing evaluation on the strains is influenced by sample state and culture conditions of the strains, and its use-cost is high.

Therefore, there is an urgent need in the related art to develop a system and a method for predicting susceptibility of genus *Klebsiella* to amikacin.

SUMMARY

In view of the above deficiencies and requirements in the related art, the disclosure aims to provide a system and a method for predicting susceptibility of genus *Klebsiella* to amikacin ($C_{22}H_{43}N_5O_{13}$).

A technical solution of the disclosure is as follows.

A system for predicting susceptibility of genus *Klebsiella* to amikacin includes: a calculating unit; the calculating unit includes: a computer-readable storage medium (e.g., a non-transitory computer-readable storage medium) stored with a computer program, the computer program is configured to, when is executed by a processor, implement a calculation method for an Exp(–k) power value, and the calculation method for the Exp(–k) power value includes the following steps:

step 1, calculating a k value according to the following formula I:

$$k = -1.446 + 0.501 \times \left(\frac{C1 - 0.018}{0.164}\right) - \quad \text{(formula I)}$$

-continued $$0.108 \times \left(\frac{C2 - 1.070}{0.075}\right) + 1.093 \times \left(\frac{C3 - 0.025}{0.226}\right) -$$

$$1.031 \times \left(\frac{C4 - 0.906}{0.413}\right) + 2.710 \times \left(\frac{C5 - 0.521}{1.082}\right); \text{ and}$$

step 2, calculating the Exp(−k) power value with an Euler's constant e as a base and a −k value as an exponential;

in the formula I, C1 represents a copy number of an arr-2 gene in to-be-predicted *Klebsiella* strains; C2 represents a copy number of an acrB gene in the to-be-predicted *Klebsiella* strains; C3 represents a copy number of an armA gene in the to-be-predicted *Klebsiella* strains; C4 represents a copy number of an oqxB gene in the to-be-predicted *Klebsiella* strains; C5 represents a copy number of a rmtB gene in the to-be-predicted *Klebsiella* strains; and the system for predicting susceptibility of genus *Klebsiella* to amikacin further includes: a result output unit; and the calculating unit is configured to transmit the Exp(−k) power value calculated by the calculating unit to the result output unit, and the result output unit is configured to identify the Exp(−k) power value and output a result.

In an embodiment, the Euler's constant e is equal to 2.718281828459045.

The result output unit outputs a drug resistance result R in response to identifying the Exp(−k) power value less than 1; and the result output unit outputs a susceptibility result S in response to identifying the Exp(−k) power value greater than or equal to 1.

The result output unit is communicated with the calculating unit by a data path, and the Exp(−k) power value calculated by the calculating unit is transmitted to the result output unit by the data path.

In an embodiment, the susceptibility result S represents that the to-be-predicted *Klebsiella* strains are susceptible to amikacin, and the drug resistance result R represents that the to-be-predicted *Klebsiella* strains are resistant to amikacin.

The system for predicting susceptibility of genus *Klebsiella* to amikacin further includes: an experimental unit and a data input unit; the experimental unit is communicated with the data input unit by a data path; the experimental unit is configured to output an experimental result, and the experimental result is transmitted to the data input unit by the data path and then is converted into independent variable data; and the data input unit is communicated with the calculating unit by another data path, and the independent variable data is transmitted to the calculating unit by the another data path. Specially, the computer-readable storage medium is non-transitory; each of the calculating unit, the result output unit, the experimental unit, and the data input unit is embodied by software stored in at least one memory and executable by at least one processor.

The independent variable data includes: values of the C1, the C2, the C3, the C4, and the C5.

In an embodiment, the experimental result includes: the copy number of the arr-2 gene in the to-be-predicted *Klebsiella* strains, the copy number of the acrB gene in the to-be-predicted *Klebsiella* strains, the copy number of the armA gene in the to-be-predicted *Klebsiella* strains, the copy number of the oqxB gene in the to-be-predicted *Klebsiella* strains, and the copy number of the rmtB gene in the to-be-predicted *Klebsiella* strains.

A method for predicting susceptibility of genus *Klebsiella* to amikacin, including:

step 1, calculating a k value according to the following formula I:

$$k = -1.446 + 0.501 \times \left(\frac{C1 - 0.018}{0.164}\right) - \quad \text{(formula I)}$$

$$0.108 \times \left(\frac{C2 - 1.070}{0.075}\right) + 1.093 \times \left(\frac{C3 - 0.025}{0.226}\right) -$$

$$1.031 \times \left(\frac{C4 - 0.906}{0.413}\right) + 2.710 \times \left(\frac{C5 - 0.521}{1.082}\right); \text{ and}$$

step 2, calculating an Exp(−k) power value with an Euler's constant e as a base and a −k value as an exponential;

in the formula I, C1 represents a copy number of an arr-2 gene in to-be-predicted *Klebsiella* strains; C2 represents a copy number of an acrB gene in the to-be-predicted *Klebsiella* strains; C3 represents a copy number of an armA gene in the to-be-predicted *Klebsiella* strains; C4 represents a copy number of an oqxB gene in the to-be-predicted *Klebsiella* strains; C5 represents a copy number of a rmtB gene in the to-be-predicted *Klebsiella* strains; and in the method for predicting susceptibility of genus *Klebsiella* to amikacin, a decision threshold includes: the Exp(−k) power value less than 1 corresponding to the genus *Klebsiella* resistant to amikacin, and the Exp(−k) power value greater than or equal to 1 corresponding to the genus *Klebsiella* susceptible to the amikacin.

In an embodiment, the Euler's constant e is equal to 2.718281828459045.

The copy number of the arr-2 gene, the copy number of the acrB gene, the copy number of the armA gene, the copy number of the oqxB gene, and the copy number of the rmtB gene in the to-be-predicted *Klebsiella* strains are obtained by second generation high-throughput sequencing.

In an embodiment, a copy number of a gene in the to-be-predicted *Klebsiella* strains is equal to $$\frac{\text{depths of contigs where the gene is located}}{\text{a genome contig depth}}.$$

In an embodiment, a genome contig is a longest contig segment assembled by SPAdes v3.13.0 assembly software from a sequencing result; the genome contig depth is a depth of the genome contig calculated by the SPAdes v3.13.0 assembly software; and the depths of contigs where the gene is located is a sum of depths on respective contigs with a copy of the gene.

In an embodiment, the respective contigs with the copy of the gene are obtained by using a blat (v.36) software and a diamond (v2.0.4.142) software to perform comparison on a coding sequencing (CDS) and a protein sequence of the gene and then performing annotation on a comprehensive antibiotic resistance database (CARD).

In an embodiment, the depths on the respective contigs with the copy of the gene are calculated by the SPAdes v3.13.0 assembly software.

According to an aspect of the disclosure, the method for predicting susceptibility of genus *Klebsiella* to amikacin is provided.

In the disclosure, after the obtained microbial samples are routinely process, sequencing necessary links, such as deoxyribonucleic acid (DNA) extraction, can be performed; and through an analysis of flow bioinformatics, characteristics related to the system for predicting susceptibility of genus *Klebsiella* in the microbial samples are obtained. Moreover, the characteristics are input the system of the disclosure to predict the susceptibility of the microbial samples. Compared with a traditional method, the method of the disclosure has the advantages of simplicity and convenience in operation, short detection time, accurate species identification, etc.

In order to effectively determine the performance of the prediction system according to the disclosure, it is necessary to establish a dataset that is not involved in the prediction system of the disclosure, and then the accuracy of the prediction system is evaluated on the dataset. Specially, the dataset is regarded as a testing set. The evaluation methods for effectiveness of the prediction system include f1-score (referred to a harmonic mean of the precision and recall), precision, recall, and a confusion matrix.

The method according to the disclosure also has the following advantages.

The disclosure utilizes the testing set to evaluate the accuracy of the system, achieving an average accuracy of 0.988, the F1-score of 0.973, and the recall of 0.973. On the one hand, the disclosure is less affected by subjective factors, such as operators, and has good detection stability. On the other hand, the disclosure realizes rapid and accurate identification of infection pathogens, quick prediction of drug susceptibility of to-be-predicted sample, auxiliary diagnosis, and reasonable standard medication treatment. Moreover, the flux of the disclosure is high, and the medical cost is reduced.

DETAILED DESCRIPTION OF EMBODIMENTS

In order to facilitate understanding of the disclosure, the disclosure will be described more fully hereinafter in embodiments.

Unless otherwise defined, all of technical and scientific terms used herein have the same meaning as commonly understood by those skilled in the related art to which the disclosure belongs. The terms used herein aim to describe illustrated embodiments only and are not intended to be a limitation for the disclosure.

Reagents used in the following embodiments, are commercially available; unless otherwise defined.

Sources of Biological Materials 171 samples used in the embodiments of the disclosure are obtained from pure cultures of *Klebsiella* strains separated from clinical blood cultures that come from Chinese Academy of Sciences in Peking Union Medical College Hospital.

All of the species (also referred to strains) used for the testing are identified as *Klebsiella* (scientific name: genus *Klebsiella*, Latin name: *Klebsiella* Trevisan, classification level: Genus) by matrix-assisted laser desorption/ionization time-of-flight mass spectrometry (MALDI-TOF MS).

In an Illumina novaseq next-generation sequencing (NGS) platform, the strains used for the testing encompass 127 samples with *Klebsiella pneumoniae*, 20 samples with *Klebsiella aerogenes*, 8 samples with *Klebsiella oxytoca*, 7 samples with *Klebsiella* quasipneumoniae, 6 samples with *Klebsiella variicola*, and 3 samples with *Klebsiella michiganensis*, which are strains of the reported *Klebsiella* species or genus *Klebsiella*.

The above-mentioned species or strains can be obtained from common pneumonia cases of *Klebsiella pneumoniae* or from Applicant's laboratory. Applicant promises to distribute the strains to the public within 20 years from the filing date of the present application for verifying the technical effects of the disclosure.

Figure 1:
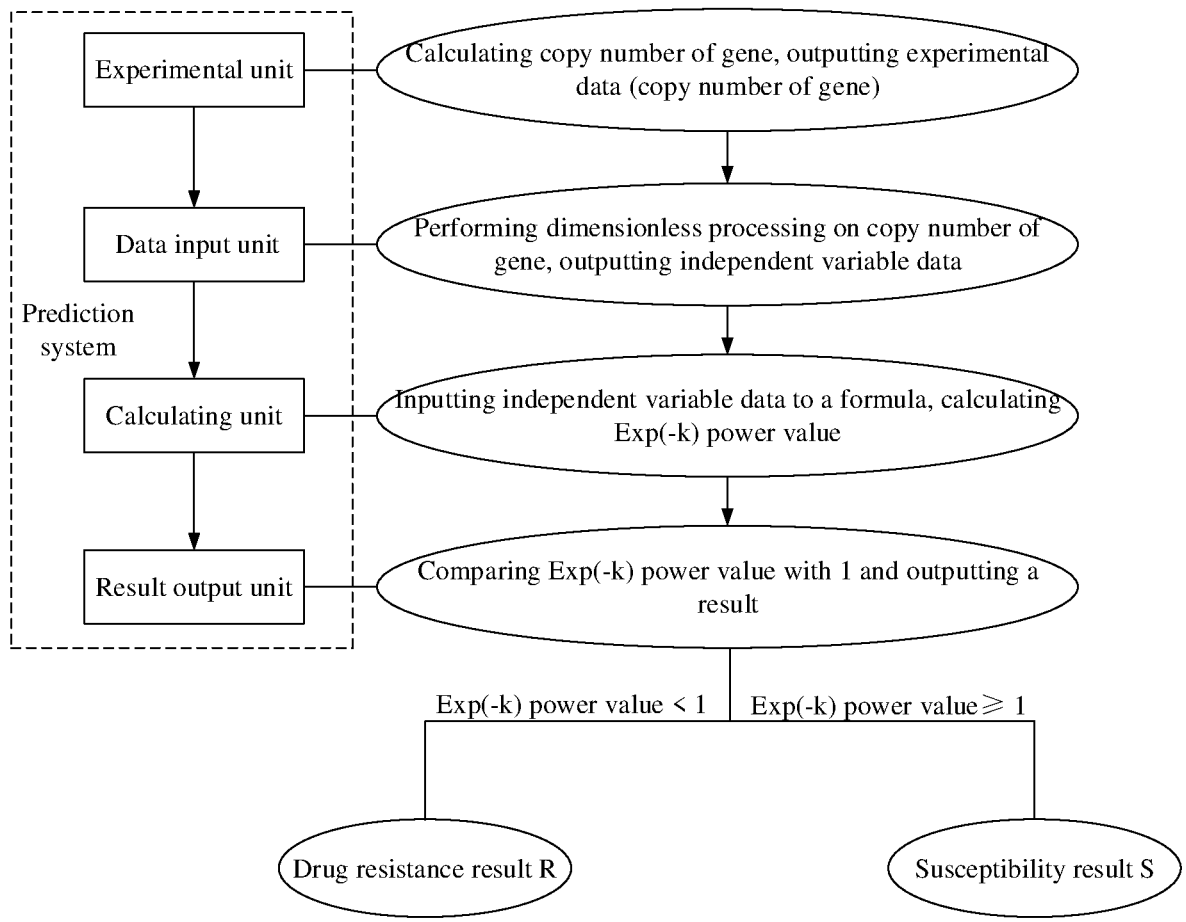
FIG. 1 illustrates a schematic structural diagram of a system for predicting susceptibility (in a dashed box) and a schematic working flowchart thereof according to some embodiments of the disclosure.
Figure 2:
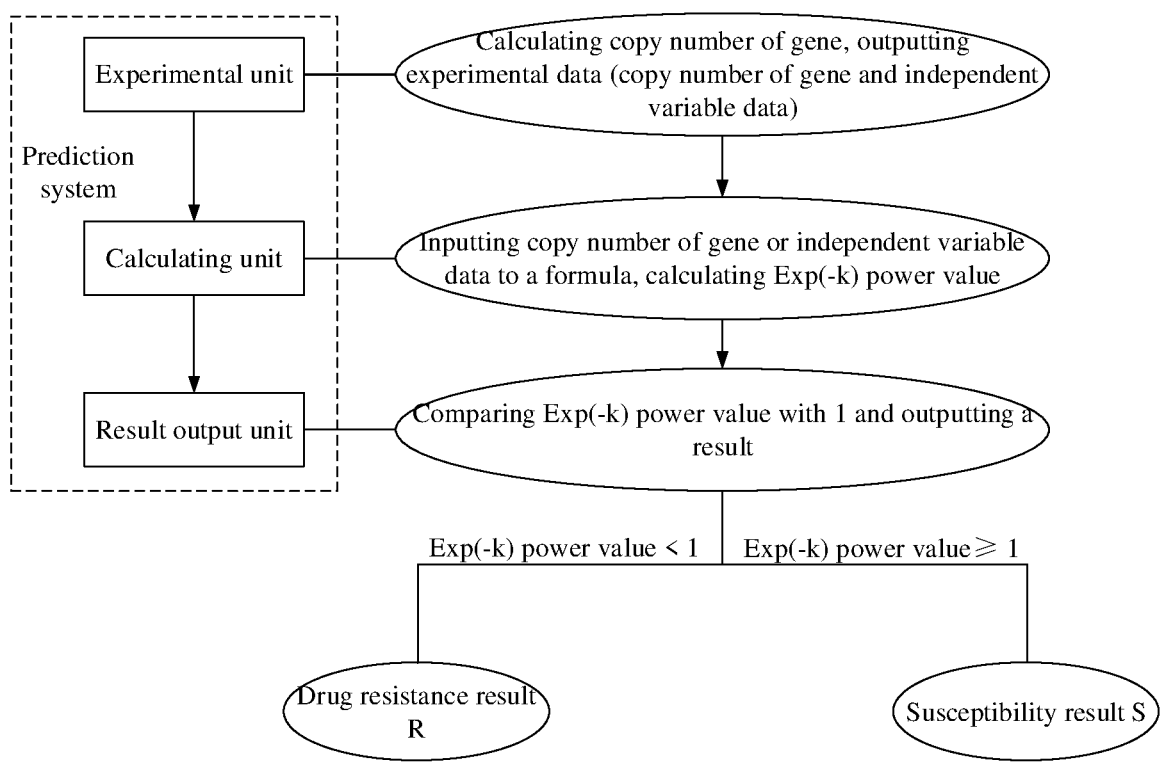
FIG. 2 illustrates a schematic structural diagram of a system for predicting susceptibility (in a dashed box) and a schematic working flowchart thereof according to some other embodiments of the disclosure.

Group 1 of Embodiments by Using a System for Predicting Susceptibility of Genus *Klebsiella* to Amikacin According to the Disclosure The group 1 of embodiments provides the system for predicting susceptibility of genus *Klebsiella* to amikacin. All of the embodiments in the group 1 have the following common features. As shown in FIG. 1 and FIG. 2, the system for predicting susceptibility of genus *Klebsiella* to amikacin includes: a calculating unit; the calculating unit includes: a computer-readable storage medium (e.g., a non-transitory computer-readable storage medium) stored with a computer program, the computer program is configured to, when is executed by a processor, implement a calculation method for an Exp(−k) power value, and the calculation method for the Exp(−k) power value includes the following steps:

step 1, calculating a k value according to the following formula I:

$$k = -1.446 + 0.501 \times \left(\frac{C1 - 0.018}{0.164}\right) - 0.108 \times \left(\frac{C2 - 1.070}{0.075}\right) + 1.093 \times \left(\frac{C3 - 0.025}{0.226}\right) - 1.031 \times \left(\frac{C4 - 0.906}{0.413}\right) + 2.710 \times \left(\frac{C5 - 0.521}{1.082}\right); \text{ and} \quad \text{(formula I)}$$

step 2, calculating the Exp(−k) power value with an Euler's constant e as a base and a −k value as an exponential; and in the formula I, C1 represents a copy number of an arr-2 gene in to-be-predicted *Klebsiella* strains; C2 represents a copy number of an acrB gene in the to-be-predicted *Klebsiella* strains; C3 represents a copy number of an armA gene in the to-be-predicted *Klebsiella* strains; C4 represents a copy number of an oqxB gene in the to-be-predicted *Klebsiella* strains; C5 represents a copy number of a rmtB gene in the to-be-predicted *Klebsiella* strains. In an embodiment, the calculating unit is embodied by a software stored in at least one memory and executable by at least one processor.

In some embodiments of the disclosure, the Euler's constant e is equal to 2.718281828459045.

In an illustrated embodiment of the disclosure, the above-mentioned genes are all genes reported in the related art, and are specifically as follows.

The arr-2 gene is a rifampin ADP-ribosyltransferase (arr-2) gene reported by Gorrie C L, Mirčeta M, Wick R R, Judd L M, Lam M M C, Gomi R, Abbott I J, Thomson N R, Strugnell R A, Pratt N F, Garlick J S, Watson K M, Hunter P C, Pilcher D V, McGloughlin S A, Spelman D W, Wyres K L, Jenney A W J, Holt K E, "Genomic dissection of *Klebsiella pneumoniae* infections in hospital patients reveals insights into an opportunistic pathogen", Nature Communications, 2022 May 31, Article 3017, volume 13, issue 1.

The acrB gene is a kind of gene of *Escherichia coli* reported by Nicolas-Chanoine M H. Mayer N, Guyot K. Dumont E, Pagès J M, "Interplay Between Membrane Permeability and Enzymatic Barrier Leads to Antibiotic-Dependent Resistance in *Klebsiella Pneumoniae*", Front Microbiol, 2018 Jun. 29, Article 1422, volume 9.

The armA gene is an aminoglycoside drug resistance (armA) gene reported by Ma L, Lin C J, Chen J H, Fung C P, Chang F Y, Lai Y K, Lin J C, Siu L K, "Widespread dissemination of aminoglycoside resistance genes armA and rmtB in *Klebsiella pneumoniae* isolates in Taiwan producing CTX-M-type extended-spectrum beta-lactamases", Taiwan Surveillance of Antimicrobial Resistance Project, 2009 January, p. 104-111, volume 53, issue 1.

The oqxB gene is a resistance-nodulation-division (RND) efflux pump that has emerged as a factor contributing to the antibiotic resistance in *Klebsiella pneumoniae* reported by Bharatham N, Bhowmik P, Aoki M, Okada U, Sharma S, Yamashita E, Shanbhag A P. Rajagopal S, Thomas T. Sarma M, Narjari R, Nagaraj S, Ramachandran V, Katagihallimath N, Datta S, Murakami S, "Structure and function relationship of OqxB efflux pump from *Klebsiella pneumoniae*", Nature Communications, 2021 Sep. 13, Article 5400, volume 12, issue 1.

The rmtB gene is an rRNA methylase (rmtB) gene reported by Wang J. Zeng Z L, Huang X Y, Ma Z B, Guo Z W, Lv L C, Xia Y B, Zeng L, Song Q H, Liu J H, "Evolution and Comparative Genomics of $F_{33}$: A-: B-Plasmids Carrying $bla_{CTX-M-55}$ or $bla_{CTX-M-65}$ in *Escherichia coli* and *Klebsiella pneumoniae* Isolated from Animals, Food Products, and Humans in China", mSphere, 2018 Jul. 18, p.e00137-18, volume 3, issue 4.

In an illustrated embodiment, as shown in FIG. 1 and FIG. 2, the system for predicting susceptibility of genus *Klebsiella* to amikacin further includes a result output unit; the result output unit is configured to output a susceptibility result or a drug resistance result; the susceptibility result indicates that the to-be-predicted *Klebsiella* strains are susceptible to amikacin, and the drug resistance result indicates that the to-be-predicted *Klebsiella* strains are resistant to amikacin. In an embodiment, the result output unit is embodied by a software stored in at least one memory and executable by at least one processor.

When the Exp(−k) power value is less than 1, the drug resistance result R is output; and when the Exp(−k) power value is greater than or equal to 1, the susceptibility result S is output.

In an illustrated embodiment, the result output unit is communicated with the calculating unit by a data path, and the Exp(−k) power value calculated by the calculating unit is transmitted to the result output unit by the data path.

In an illustrated embodiment, as shown in FIG. 1, the system for predicting susceptibility of genus *Klebsiella* to amikacin further includes: an experimental unit and a data input unit; the experimental unit is communicated with the data input unit by a data path; the experimental unit is configured to output an experimental result, and the experimental result is transmitted to the data input unit by the data path and then is converted into independent variable data; and the data input unit is communicated with the calculating unit by another data path, and the independent variable data is transmitted to the calculating unit by the another data path. In an embodiment, each of the experimental unit and the data input unit is embodied by a software stored in at least one memory and executable by at least one processor.

Specially, the data path is a data transmission carrier well known to those skilled in the fields of computer and electronics. The data path is selected from a wired form or a wireless form, such as a wired path, a circuit, or a wireless path, wireless fidelity (Wi-Fi) connection, a wireless channel, etc.

In an illustrated embodiment, the independent variable data includes: values of the C1, the C2, the C3, the C4, and the C5.

In an illustrated embodiment, the experimental result includes: the copy number of the arr-2 gene in the to-be-predicted *Klebsiella* strains, the copy number of the acrB gene in the to-be-predicted *Klebsiella* strains, the copy number of the armA gene in the to-be-predicted *Klebsiella* strains, the copy number of the oqxB gene in the to-be-predicted *Klebsiella* strains, and the copy number of the rmtB gene in the to-be-predicted *Klebsiella* strains.

The number of the copy of the specific gene in the determined strains is known to the technicians, which is realized by those skilled in the fields of molecular biology, bioinformatics, etc. through conventional technical means, e.g., sequencing and bioinformatics analysis. The arr-2, acrB, armA, oqxB, and rmtB genes involved in the experimental result output by the experimental unit of the system according to the disclosure are the known genes reported in the related art, and the gene information and the primary structure sequence thereof can be queried by national center for biotechnology information (NCBI) website or other known bioinformatics databases. The copy number of each gene in the to-be-predicted *Klebsiella* strains can be obtained by performing whole genome sequencing on the to-be-predicted *Klebsiella* strains.

In some other illustrated embodiments, the copy numbers of the arr-2, acrB, armA, oqxB, and rmtB genes in the to-be-predicted *Klebsiella* strains are obtained by second generation high-throughput sequencing.

In an illustrated embodiment, a copy number of a specific gene in the to-be-predicted *Klebsiella* strains is equal to $$\frac{\text{depths of contigs where the gene is located}}{\text{a genome contig depth}}.$$

In an illustrated embodiment, a genome contig is a longest contig segment assembled by SPAdes v3.13.0 assembly software (containing Genome Assembly Algorithm) from a sequencing result; the genome contig depth is a depth of the genome contig calculated by the SPAdes v3.13.0 assembly software; and the depths of contigs where the gene is located is a sum of depths on respective contigs with a copy of the gene.

In an illustrated embodiment, the respective contigs with the copy of the gene are obtained by using blat (v.36) software (referred to a bioinformatics software tool which performs rapid mRNA/DNA and cross-species protein alignments) and diamond (v2.0.4.142) software (referred to a sequence aligner for protein and translated DNA searches) to perform comparison on a coding sequencing (CDS) and a protein sequence of the gene and then performing annotation on a comprehensive antibiotic resistance database (CARD).

In an illustrated embodiment, the depths on respective contigs with the copy of the gene are calculated by using the SPAdes v3.13.0 assembly software.

The second generation high-throughput sequencing is familiar to those skilled in the related art, and the second generation high-throughput sequencing is a conventional technical means familiar to those skilled in the related art to obtain the copy number of the specific gene.

In some illustrated embodiments, a method for calculating the copy number of the gene is as follows.

The to-be-predicted *Klebsiella* strains are sequenced by using the second generation high-throughput sequencing. An average sequencing depth is about 150× (referred to a ratio between a total number of nucleobase obtained by the sequencing and a genome), and a sequencing volume of the genus *Klebsiella* is approximately 1 G. A depth of a contig calculated by the SPAdes v3.13.0 assembly software during the assembly is used as a standard, and the longest contig segment is determined as the genome segment, and then gene prediction is performed on the genome contig by using prokka (1.14.6) software to obtain coding sequencings (CDS) and protein sequences of all genes on the genome contig. Thereafter, the obtained coding sequencings and the protein sequences of all genes are used the blat (v.36) software and the diamond (v2.0.4.142) software, respectively to compare with the corresponding data in the CARD, and when a similarity of the sequence result is greater than 90%, the corresponding sequencing is regarded as a positive sequence, thereby obtaining annotation results of all of drug-resistant genes. The copy numbers of all the genes on the contig are calculated according to the following formula II:

$$\text{copy numbers of all the genes on the contig} = \frac{\text{the depth of the contig}}{\text{the genome contig depth}}. \quad \text{(formula II)}$$

If a gene has two or more genome copies on different contigs or the same contig, the final copy number of this gene is equal to the sum of all the calculated copies of the gene. An example of a calculation method is as follows:
assuming that arr-2 gene has only one copy on all contigs, the copy number of the arr-2 gene is as follows:

$$\text{copy number of } arr-2 \text{ gene} = \frac{\text{a depth of a contiq where the } arr-2 \text{ gene is located}}{\text{a genome contig depth}};$$

assuming that there are two copies of the arr-2 gene on one contig, and there is no copy on other contigs, and the copy number of the arr-2 gene is as follows:

$$\text{copy number of } arr-2 \text{ gene} = 2 \times \frac{\text{the depth of the contig where the } arr-2 \text{ gene is located}}{\text{the genome contig depth}};$$

and
assuming that the arr-2 gene has one copy on contig 1 and contig 2, respectively, and there is no copy on another contigs, and the copy number of the arr-2 gene is as follows:

$$\text{copy number of } arr-2 \text{ gene} =$$

-continued
$$\frac{\text{a depth of a contig 1 where the } arr-2 \text{ gene is located}}{\text{the genome contig depth}} +$$
$$\frac{\text{a depth of a contig 2 where the } arr-2 \text{ gene is located}}{\text{the genome contig depth}}.$$

In an illustrated embodiment, the result output unit, the experimental unit, and the data input unit are each provided with a computer-readable storage medium stored with a computer program.

In some embodiments, when the computer program stored on the computer-readable storage medium of the result output unit is executed by the processor, the Exp(−k) power value is compared with 1 to output a corresponding result (i.e., the drug resistance result R and the susceptibility result S). Namely, when the Exp(−k) power value is less than 1, the result output unit outputs the drug resistance result R; and when the Exp(−k) power value is greater than or equal to 1, the result output unit outputs the susceptibility result S.

In some other embodiments, when the computer program stored on the computer-readable storage medium of the experimental unit is executed by the processor, the copy number of the corresponding gene is calculated.

The calculation for the copy number of the gene is a conventional technical means well known to those skilled in the related art, and is specifically implemented according to the following steps:
step 1, obtaining the genome contig depth by adopting a maximum genome contig depth calculated by the SPAdes v3.13.0 assembly software;
step 2, obtaining the respective contigs with the copy of the gene by using the blat (v.36) software and the diamond (v2.0.4.142) software to perform comparison on the cds and the protein sequence of the gene and then performing annotation on the CARD;
step 3, calculating the depths on the respective contigs with the copy of the gene by using the SPAdes v3.13.0 assembly software;
step 4, summing up the depths on respective contigs with the copy of the gene to obtain the depths of contigs where the gene is located; and
step 5, obtaining the copy number of the corresponding gene by the following formula:

$$\text{copy number of the gene in the to-be-predicted } klebsiella \text{ strains} =$$
$$\frac{\text{depths of contigs where the gene is located}}{\text{a genome contig depth}}.$$

In some embodiments, the computer program stored on the computer-readable storage medium of the data input unit implements dimensionless processing on the copy number of the gene when executed by the processor.

The dimensionless processing means: removing a data dimension or a data unit from the copy number of the gene to obtain a dimensionless numerical value, i.e., the independent variable data. In general, the data dimension or data unit of the copy number of the gene is copy, number of individuals, or copies.

In some other embodiments, as shown in FIG. 2, the system for predicting susceptibility of genus *Klebsiella* to amikacin cannot include the data input unit, and the experimental unit is directly connected to the calculating unit by the data path, so that the calculated copy number of the gene or the independent variable data calculated by the experimental unit can be directly input into the calculating unit to calculate the Exp(−k) power value.

Group 2 of Embodiments by Using a Method for Predicting Susceptibility of Genus *Klebsiella* to Amikacin According to the Disclosure The group 2 of embodiments provides the method for predicting susceptibility of genus *Klebsiella* to amikacin. All of the embodiments in the group 2 have the following common features. Specially, the method includes the following steps:

step 1, calculating a k value according to the following formula I:

$$k = -1.446 + 0.501 \times \left(\frac{C1 - 0.018}{0.164}\right) - \\ 0.108 \times \left(\frac{C2 - 1.070}{0.075}\right) + 1.093 \times \left(\frac{C3 - 0.025}{0.226}\right) - \\ 1.031 \times \left(\frac{C4 - 0.906}{0.413}\right) + 2.710 \times \left(\frac{C5 - 0.521}{1.082}\right); \text{ and}$$
(formula I)

step 2, calculating an Exp(−k) power value with an Euler's constant e as a base and a −k value as an exponential;

in the formula I, C1 represents a copy number of an arr-2 gene in to-be-predicted *Klebsiella* strains; C2 represents a copy number of an acrB gene in the to-be-predicted *Klebsiella* strains; C3 represents a copy number of an armA gene in the to-be-predicted *Klebsiella* strains; C4 represents a copy number of an oqxB gene in the to-be-predicted *Klebsiella* strains; C5 represents a copy number of a rmtB gene in the to-be-predicted *Klebsiella* strains; and a decision threshold includes: the Exp(−k) power value less than 1 corresponding to the genus *Klebsiella* resistant to amikacin, and the Exp(−k) power value greater than or equal to 1 corresponding to the genus *Klebsiella* susceptible to the amikacin.

In the above formula I, the Euler's constant e is a mathematical constant, is a base of a natural logarithm, and is also named as a natural constant, a natural base, or an Euler's constant. Moreover, the e is infinite non-repeating decimals, which is familiar to those skilled in the field of mathematics, and the e is equal to 2.718281828459045.

In some embodiments of the disclosure, a value of the natural constant e is 2.718281828459045.

In some illustrated embodiments, the copy numbers of the arr-2, acrB, armA, oqxB, and rmtB genes in the to-be-predicted *Klebsiella* strains are obtained by second generation high-throughput sequencing.

In an illustrated embodiment, a copy number of a gene in the to-be-predicted $$klebsiella \text{ strains is equal to} \frac{\text{depths of contigs where the gene is located}}{\text{a genome contig depth}}.$$

In an illustrated embodiment, a genome contig is a longest contigs segment assembled by SPAdes v3.13.0 assembly software from a sequencing result; the genome contig depth is a depth of the genome contig calculated by the SPAdes v3.13.0 assembly software; and the depths of contigs where the gene is located is a sum of depths on respective contigs with a copy of the gene.

In an illustrated embodiment, the respective contigs with the copy of the gene are obtained by using blat (v.36) software and diamond (v2.0.4.142) software to perform comparison on a coding sequencing (CDS) and a protein sequence of the gene and then performing annotation on a CARD.

In an illustrated embodiment, the depths on respective contigs with the copy of the gene are calculated by using the SPAdes v3.13.0 assembly software.

The second generation high-throughput sequencing has a conventional technical meaning well known to those skilled in the related art, the second generation high-throughput sequencing is a conventional technical means familiar to those skilled in the related art to obtain the copy number of the specific gene.

In some illustrated embodiments, a method for calculating the copy number of the gene is as follows.

The to-be-predicted *Klebsiella* strains are sequenced by using the second generation high-throughput sequencing. An average sequencing depth is about 150 ×, and a sequencing volume of the genus *Klebsiella* is approximately 1 G. A depth of a contig calculated by the SPAdes v3.13.0 assembly software during the assembly is used as a standard, and the longest contig segment is determined as the genome segment, and then gene prediction is performed on the genome contig by using prokka (1.14.6) software to obtain coding sequencings (CDS) and protein sequences of all genes on the genome contig. Thereafter, the obtained coding sequencings and the protein sequences of all genes are used the blat (v.36) software and the diamond (v2.0.4.142) software, respectively to compare with the corresponding data in the CARD, and when a similarity of the sequence result is greater than 90%, the corresponding sequencing is regarded as a positive sequence, thereby obtaining annotation results of all of drug-resistant genes. The copy numbers of all the genes on the contig are calculated according to the following formula II:

$$\text{copy numbers of all the genes on the contig} = \frac{\text{the depth of the contig}}{\text{the genome contig depth}}.$$
(formula II)

If a gene has two or more genome copies on different contigs or the same contig, the final copy number of this gene is equal to the sum of all the calculated copies of the gene. An example of a calculation method is as follows:

assuming that arr-2 gene has only one copy on all contigs, the copy number of the arr-2 gene is as follows:

$$\text{copy number of } arr-2 \text{ gene} = \\ \frac{\text{a depth of a contig where the } arr-2 \text{ gene is located}}{\text{a genome contig depth}};$$

assuming that there are two copies of the arr-2 gene on one contig, and there is no copy on other contigs, and the copy number of the arr-2 gene is as follows:

$$\text{copy number of } arr-2 \text{ gene} = \\ 2 \times \frac{\text{the depth of the contig where the } arr-2 \text{ gene is located}}{\text{the genome contig depth}}; \text{ and}$$

assuming that the arr-2 gene has one copy on contig 1 and contig 2, respectively, and there is no copy on other contigs, and the copy number of the arr-2 gene is as follows:

$$\text{copy number of } arr-2 \text{ gene} = \frac{\text{a depth of a contig 1 where the } arr-2 \text{ gene is located}}{\text{the genome contig depth}} + \frac{\text{a depth of a contig 2 where the } arr-2 \text{ gene is located}}{\text{the genome contig depth}}.$$

Performance Evaluation of the Embodiments, the Prediction System, and the Prediction Method According to the Disclosure The prediction system of the disclosure is evaluated by using 171 clinical samples, and classification results of the 171 clinical samples by using broth microdilution method are compared with prediction results of the 171 clinical samples provided by the prediction system shown in Table 1 below. Specially, S in the lower table indicates the susceptibility result, and R indicates the drug resistance result.

TABLE 1

| Sample | Exp(-k) | Predicted drug susceptibility result | Valiafation result of broth microdilution method |
|---|---|---|---|
| s1 | 36.03703704 | S | S |
| s2 | 18.23076923 | S | S |
| s3 | 0 | R | R |
| s4 | 57.82352941 | S | S |
| s5 | 0.046025105 | R | R |
| s6 | 0.002004008 | R | R |
| s7 | 23.3902439 | S | S |
| s8 | 27.57142857 | S | S |
| s9 | 37.46153846 | S | S |
| s10 | 42.47826087 | S | S |
| s11 | 34.71428571 | S | S |
| s12 | 40.66666667 | S | S |
| s13 | 37.46153846 | S | S |
| s14 | 27.57142857 | S | S |
| s15 | 37.46153846 | S | S |
| s16 | 0.213592233 | R | R |
| s17 | 0.068376068 | R | R |
| s18 | 0.006036217 | R | R |
| s19 | 0.030927835 | R | R |
| s20 | 0.004016064 | R | R |
| s21 | 0.024590164 | R | R |
| s22 | 0.184834123 | R | R |
| s23 | 27.57142857 | S | S |
| s24 | 0.002004008 | R | R |
| s25 | 36.03703704 | S | S |
| s26 | 46.61904762 | S | S |
| s27 | 31.25806452 | S | S |
| s28 | 24.64102564 | S | S |
| s29 | 37.46153846 | S | S |
| s30 | 26.77777778 | S | S |
| s31 | 26.02702703 | S | S |
| s32 | 44.45454545 | S | S |
| s33 | 29.3030303 | S | S |
| s34 | 22.80952381 | S | S |
| s35 | 26.77777778 | S | S |
| s36 | 0.02145046 | R | R |
| s37 | 25.31578947 | S | S |
| s38 | 44.45454545 | S | S |
| s39 | 36.03703704 | S | S |
| s40 | 36.03703704 | S | S |
| s41 | 34.71428571 | S | S |
| s42 | 31.25806452 | S | S |
| s43 | 0.091703057 | R | R |
| s44 | 26.02702703 | S | S |
| s45 | 0.107419712 | R | R |
| s46 | 30.25 | S | S |
| s47 | 0.111111111 | R | R |
| s48 | 31.25806452 | S | S |
| s49 | 33.48275862 | S | S |
| s50 | 0.225490196 | R | R |
| s51 | 0.004016064 | R | R |
| s52 | 2.164556962 | S | S |
| s53 | 34.71428571 | S | S |
| s54 | 0.003009027 | R | R |
| s55 | 27.57142857 | S | S |
| s56 | 40.66666667 | S | S |
| s57 | 1.83286119 | S | S |
| s58 | 33.48275862 | S | S |
| s59 | 37.46153846 | S | S |
| s60 | 2.225806452 | S | R |
| s61 | 32.33333333 | S | S |
| s62 | 30.25 | S | S |
| s63 | 46.61904762 | S | S |
| s64 | 27.57142857 | S | S |
| s65 | 40.66666667 | S | S |
| s66 | 32.33333333 | S | S |
| s67 | 2.048780488 | S | S |
| s68 | 40.66666667 | S | S |
| s69 | 0 | R | R |
| s70 | 25.31578947 | S | S |
| s71 | 49 | S | S |
| s72 | 36.03703704 | S | S |
| s73 | 18.60784314 | S | S |
| s74 | 33.48275862 | S | S |
| s75 | 0.136363636 | R | R |
| s76 | 34.71428571 | S | S |
| s77 | 36.03703704 | S | S |
| s78 | 32.33333333 | S | S |
| s79 | 0.001001001 | R | R |
| s80 | 0.041666667 | R | R |
| s81 | 30.25 | S | S |
| s82 | 34.71428571 | S | S |
| s83 | 31.25806452 | S | S |
| s84 | 36.03703704 | S | S |
| s85 | 40.66666667 | S | S |
| s86 | 29.3030303 | S | S |
| s87 | 28.41176471 | S | S |
| s88 | 34.71428571 | S | S |
| s89 | 18.23076923 | S | S |
| s90 | 61.5 | S | S |
| s91 | 20.73913043 | S | S |
| s92 | 30.25 | S | S |
| s93 | 44.45454545 | S | S |
| s94 | 23.3902439 | S | S |
| s95 | 27.57142857 | S | S |
| s96 | 34.71428571 | S | S |
| s97 | 37.46153846 | S | S |
| s98 | 39 | S | S |
| s99 | 0.111111111 | R | R |
| s100 | 26.77777778 | S | S |
| s101 | 28.41176471 | S | S |
| s102 | 32.33333333 | S | S |
| s103 | 32.33333333 | S | S |
| s104 | 54.55555556 | S | S |
| s105 | 2.921568627 | S | S |
| s106 | 29.3030303 | S | S |
| s107 | 21.22222222 | S | S |
| s108 | 36.03703704 | S | S |
| s109 | 26.77777778 | S | S |
| s110 | 0.062699256 | R | R |
| s111 | 28.41176471 | S | S |
| s112 | 0.001001001 | R | R |
| s113 | 28.41176471 | S | S |
| s114 | 0.002004008 | R | R |
| s115 | 27.57142857 | S | S |
| s116 | 40.66666667 | S | S |
| s117 | 32.33333333 | S | S |
| s118 | 39 | S | S |
| s119 | 30.25 | S | S |
| s120 | 34.71428571 | S | S |
| s121 | 25.31578947 | S | S |
| s122 | 39 | S | S |

TABLE 1-continued

| Sample | Exp(-k) | Predicted drug susceptibility result | Valiafation result of broth microdilution method |
|---|---|---|---|
| s123 | 0.002004008 | R | R |
| s124 | 24.64102564 | S | S |
| s125 | 19.40816327 | S | S |
| s126 | 21.72727273 | S | S |
| s127 | 29.3030303 | S | S |
| s128 | 46.61904762 | S | S |
| s129 | 37.46153846 | S | S |
| s130 | 34.71428571 | S | S |
| s131 | 0.004016064 | R | R |
| s132 | 0.333333333 | R | R |
| s133 | 22.80952381 | S | S |
| s134 | 0 | R | R |
| s135 | 29.3030303 | S | S |
| s136 | 39 | S | S |
| s137 | 34.71428571 | S | S |
| s138 | 36.03703704 | S | S |
| s139 | 0.002004008 | R | R |
| s140 | 30.25 | S | S |
| s141 | 2.086419753 | S | S |
| s142 | 27.57142857 | S | S |
| s143 | 29.3030303 | S | S |
| s144 | 54.55555556 | S | S |
| s145 | 21.72727273 | S | S |
| s146 | 40.66666667 | S | S |
| s147 | 39 | S | S |
| s148 | 25.31578947 | S | S |
| s149 | 46.61904762 | S | S |
| s150 | 22.80952381 | S | S |
| s151 | 20.27659574 | S | S |
| s152 | 40.66666667 | S | S |
| s153 | 23.3902439 | S | S |
| s154 | 0.314060447 | R | S |
| s155 | 25.31578947 | S | S |
| s156 | 28.41176471 | S | S |
| s157 | 31.25806452 | S | S |
| s158 | 30.25 | S | S |
| s159 | 36.03703704 | S | S |
| s160 | 30.25 | S | S |
| s161 | 40.66666667 | S | S |
| s162 | 16.54385965 | S | S |
| s163 | 0 | R | R |
| s164 | 0 | R | R |
| s165 | 0.001001001 | R | R |
| s166 | 0.003009027 | R | R |
| s167 | 30.25 | S | S |
| s168 | 33.48275862 | S | S |
| s169 | 40.66666667 | S | S |
| s170 | 24 | S | S |
| s171 | 0.014198783 | R | R |

The result data obtained by the testing generates a confusion matrix as follows in Table 2.

TABLE 2

| Confusion matrix | | Prediction result | |
|---|---|---|---|
| | | R | S |
| Real result | R | 36 | 1 |
| | S | 1 | 133 |

True Positive (TP) is assumed to represent the number of true positive samples, False Positive (FP) is assumed to represent the number of false positive samples, False Negative (FN) is assumed to represent the number of false negative samples, and True Negative (TN) is assumed to the number of true negative samples. Precision refers to the portion of the true positive samples in the positive samples (i.e., the true positive samples and the false positive samples) determined by the classifier. A rate for the recall refers to the proportion of the samples predicted as positive in the total positive samples. Accuracy refers to the portion of correct predictions made by the classifier on the entire testing samples. F1-Score illustrates the harmonic mean of the precision and recall, with a maximum of 1 and a minimum of 0. Specially, calculation results of the above evaluation indices are as follows:

$$precission = \frac{TP}{TP+FP} = \frac{36}{36+1} = 0.973;$$

$$recall = \frac{TP}{TP+FN} = \frac{36}{36+1} = 0.973;$$

$$accuracy = \frac{TP+TN}{TP+FP+TN+FN} = \frac{36+133}{36+1+133+1} = 0.988;$$

$$F1 = \frac{2 \times precision \times recall}{precission + recall} = 0.973.$$

The above embodiments only express the implementation modes of the disclosure, and the description thereof is more specific and detailed, but cannot be understood as a limitation on the scope of the disclosure. It should be noted that, for those skilled in the related art, several variations and improvements may be made without departing from the concept of the disclosure, which shall fall within the scope of the protection of the disclosure. Therefore, the scope of the protection of the disclosure shall be subject to the description of the disclosure.

What is claimed is:

1. A method for predicting susceptibility of genus *Klebsiella* to amikacin, comprising:

step 1, calculating a k value according to the following formula I:

$$k = -1.446 + 0.501 \times \left(\frac{C1-0.018}{0.164}\right) - \qquad \text{(formula I)}$$
$$0.108 \times \left(\frac{C2-1.070}{0.075}\right) + 1.093 \times \left(\frac{C3-0.025}{0.226}\right) -$$
$$1.031 \times \left(\frac{C4-0.906}{0.413}\right) + 2.710 \times \left(\frac{C5-0.521}{1.082}\right); \text{and}$$

step 2, calculating an Exp(−k) power value with an Euler's constant e as a base and a −k value as an exponential;

wherein in the formula I, C1 represents a copy number of an arr-2 gene in *Klebsiella* strains; C2 represents a copy number of an acrB gene in the *Klebsiella* strains; C3 represents a copy number of an armA gene in the *Klebsiella* strains; C4 represents a copy number of an oqxB gene in the *Klebsiella* strains; C5 represents a copy number of a rmtB gene in the *Klebsiella* strains; and wherein a decision threshold comprises: the Exp(−k) power value less than 1 corresponding to the genus *Klebsiella* resistant to the amikacin, and the Exp(−k) power value greater than or equal to 1 corresponding to the genus *Klebsiella* susceptible to the amikacin; and the method further comprises:

administering the amikacin to a patient in a medication treatment based on the decision threshold.

2. The method for predicting susceptibility of genus *Klebsiella* to amikacin according to claim 1, wherein the Euler's constant e is equal to 2.718281828459045.

3. The method for predicting susceptibility of genus *Klebsiella* to amikacin according to claim 1, wherein the copy number of the arr-2 gene, the copy number of the acrB gene, the copy number of the armA gene, the copy number of the oqxB gene, and the copy number of the rmtB gene in the *Klebsiella* strains are obtained by second generation high-throughput sequencing.

4. The method for predicting susceptibility of genus *Klebsiella* to amikacin according to claim 3, wherein a copy number of a gene in the *klebsiella* strains is equal to $$\frac{\text{depths of contigs where the gene is located}}{\text{a genome contig depth}}.$$

5. The method for predicting susceptibility of genus *Klebsiella* to amikacin according to claim 4, wherein a genome contig is a longest contig segment assembled by a SPAdes v3.13.0 assembly software from a sequencing result;

wherein the genome contig depth is a depth of the genome contig calculated by the SPAdes v3.13.0 assembly software; and wherein the depths of contigs where the gene is located is a sum of depths on respective contigs with a copy of the gene.

6. The method for predicting susceptibility of genus *Klebsiella* to amikacin according to claim 5, wherein the respective contigs with the copy of the gene are obtained by using a blat software and a DIAMOND software to perform comparison on a coding sequencing and a protein sequence of the gene and then performing annotation on a comprehensive antibiotic resistance database (CARD).

7. The method for predicting susceptibility of genus *Klebsiella* to amikacin according to claim 5, wherein the depths on the respective contigs with the copy of the gene are calculated by the SPAdes v3.13.0 assembly software.

* * * * *